United States Patent [19]

Tazaki et al.

[11] Patent Number: 5,317,102
[45] Date of Patent: May 31, 1994

[54] 3,6-DIAMINO-2,5-PYRAZINEDICARBONI-TRILE

[75] Inventors: Seiji Tazaki; Tomio Yagihara, both of Kurashiki; Nobuo Matsui, Odawara; Atsushi Yanagisawa, Odawara; Takakazu Kojima, Odawara, all of Japan

[73] Assignee: Nippon Soda Co., Ltd., Tokyo, Japan

[21] Appl. No.: 927,258

[22] Filed: Aug. 7, 1992

Related U.S. Application Data

[62] Division of Ser. No. 689,052, filed as PCT/JP90/01092, Aug. 29, 1989.

[30] Foreign Application Priority Data

Aug. 31, 1989 [JP] Japan .................................. 1-223215
Mar. 13, 1990 [JP] Japan .................................. 2-59935

[51] Int. Cl.$^5$ ........................................... C07D 241/26
[52] U.S. Cl. ..................................... 544/336; 558/396; 558/438
[58] Field of Search ........................................ 544/336

[56] References Cited

U.S. PATENT DOCUMENTS 3,674,749  7/1972  Craven ................................ 544/336
3,763,161  10/1973  Hartter ................................ 544/336
3,928,351  12/1975  Donald ................................ 544/336

FOREIGN PATENT DOCUMENTS

88/01264  2/1988  World Int. Prop. O. .

OTHER PUBLICATIONS

Begland et al, *J. Org. Chem.* 39, p. 1235 (1974).
*The Pyrazines* by G. B. Barlin, vol. 41, of *The Chemistry of Heterocyclic Compounds,* pp. 35–36, 98, 126, 128, 129, 280 (1982).

*Primary Examiner*—Emily Bernhardt
*Attorney, Agent, or Firm*—Joseph C. Mason, Jr.; George B. Oujevolk; Ronald E. Smith

[57] ABSTRACT

This invention relates to 3,6-diamino-2,5-pyrazinedicarbonitrile which is a red crystal and yellowish green fluorescent substance and the methods of preparation from compounds represented by formula [I],

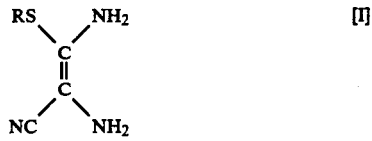

(wherein R are aryl, alkyl, aralkyl or alkenyl or may be substituted), as a starting material, under acidic condition in the presence of oxygen.

8 Claims, No Drawings

3,6-DIAMINO-2,5-PYRAZINEDICARBONITRILE

This is a divisional of copending application Ser. No. 07/689,052 filed on Apr. 29, 1991, filed as PCT/JP90/01092, Aug. 29, 1990 now abandoned.

TECHNICAL FIELD

This invention relates to 3,6-diamino-2,5-pyrazinedicarbonitrile which is a new pyrazine derivative having the formula [II] and its preparation methods.

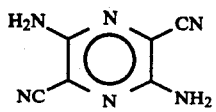

[II]

The 3,6-diamino-2,5-pyrazinedicarbonitrile is a red crystal and yellowish green fluorescenct substance. It can be applied as fluorescent dyestuff, light energy conversion material and also a useful intermediate to synthesize compounds including such as pteridine ring.

BACKGROUND ART

Pyrazines are one of the most important heterocycle containing nitrogen. They are widely used for agricultural, pharmaceutical, cosmetic, polymeric chemicals and functional materials. Amino and cyano groups are especially important as the substituents, because of their potentiality to convert into other functional groups and to introduce various derivatives. Therefore, pyrazines substituted with both these groups are prospective starting materials.

Since diaminomaleonitrile (abbreviated as DAMN, hereafter) and its derivatives are commonly based starting materials in technical fields, further development of simple synthetic process from DAMN to the useful pyrazines has been expected.

Pyrazine derivatives, substituted by both amino and cyano groups such as 6-amino-2,3,5-pyrazinetricarbonitrile, 5,6-diamiono-2,3-pyrazinedicarbonitrile and 3,5-diamino-2,6-pyrazinedicarbonitrile etc., have been synthesized from DAMN or its homologues as the starting materials. (J. Org. Chem., 39, 1235 (1974) and Japanese Patent Application No. Sho 63-75909).

On the other hand, the example of the 3,6-diamino-2,5-pyrazinedicarbonitrile having symmetric structure was depicted in U.S. Pat. No. 3,674,749 as the starting material for polymers. However, the compound mentioned in the specification text was quite different from the one shown in the figure. Furthermore, in the description neither of the physical properties, nor the method of preparation of these examples of use of the pyrazine carbonitrile have been confirmed.

DISCLOSURE OF INVENTION 2,3-diamino-3-(phenylthio)acrylonitrile (abbreviated as DAAN, hereafter), which is a related substance of DAMN, is readily derived from hydrogen cyanide and diphenyl disulfide. The inventors have noted the powerful emission of fluorescence in the course of the research on the synthesis of new heterocyclic compounds from DAAN, traced the fluroescent compound formed, identified it as 3,6-diamino-2,5-pyrazinedicarbonitrile and established a simple method of synthesizing the compound by further investigations.

Objects in the invention are "the invented compound" 3,6-diamino-2,5-pyrazinedicarbonitrile which is a new heterocyclic compound, and its preparation particularly by the reaction of the compounds which are homologues of DAAN, represented formula [I], wherein R is aryl, alkyl, aralkyl or alkenyl and may be substituted.

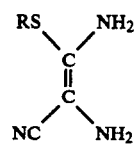

[I]

BEST MODES FOR CARRYING OUT THE INVENTION

A detailed description of the invention follows.

The compounds of general formula [I] as starting materials are able to be readily synthesized by known methods as described in WO 88/01264.

The compounds represented by general formula [I] are reacted under the condition of (a) in an acid solution or (b) in a solution of their acid salt solutions.

The reaction (a) is generally carried out in organic solvents or in mixed solvents of organic solvents and water in the presence of an acid or a buffer solution for pH adjustment at 0°–30° C. for one to several hours under atmospheric pressure, with bubbling air if necessary. Hydrocarbons such as benzene, toluene and xylene; nitriles such as acetonitrile; halogenated hydrocarbons such as chloroform and dichloromethane; esters such as ehtyl acetate; alcohols such as methanol and ethanol, ketones such as acetone and methyl ethyl ketone, ethers such as tetrahydrofuran, dioxane and 1,2-dimethoxyethane, dimethylformamide and dimethyl sulfoxide are applicable, or, these mixtures are also adoptable as the reaction solvents. Acidity of the reaction system, that is, pH should be kept at 1–5, and it is particularly desirable to adjust it to 2–4. Although any acid either inorganic or organic can be used to adjust pH, it is preferable to use a suitabely selected buffer solutions. Additionally, the reaction system should be kept under oxidative atomosphere, because the reactions concerning the invention are interpreted to be oxidative dimerization condensation. It is recommended that air or oxygen be bubbled into the reaction system, although mere contact with atmospheric oxygen is acceptable.

In the case of reaction (b), that is, applying the salts of compounds represented at general formula [I] with acids, polar solvents dissolving the salts, for example, acetonitrile, alcohols, dimethylformamide, dimethyl sulfoxide and their mixtures which may contain water are selected for the reaction.

The reaction is completed for 2–12 hours, preferably with bubbling air into the system to positively keep it in an oxidative state, the same as in the case of reaction (a).

Inorganic acid salts such as hydrochloride, sulfate and nitrate, as well as organic salts such as p-toluenesulfonate, oxalate and picrate can be given as the examples. Furthermore, acids such as trichloroacetic acid and perchloric acid can be utilized in the reaction system although their salts are not likely to be isolated.

In both the cases of the (a) and (b) reaction systems, the proposed compound (the 3,6-diamino-2,5-pyrazinedicarbonitrile) can be obtained by the usual work up after the completion of reactions.

Identification of the product is confirmed to compare IR, NMR and Mass Spectrometry with known isomers of 3,6-diamino-2,5-pyrazinedicarbonitrile compound.

The following illustrative examples are given for a better understanding of the invention.

EXAMPLE 1

To a solution with a pH adjusted to be 3.0 with 150 ml of the buffer solution which consisted of 0.1M citric acid and 0.1M sodium citrate and 150 ml of water was added a solution of 400 mg of DAAN in 45 ml of dimethoxyethane (DME). The reaction mixture was allowed to stand for 5 hours at room temperature. Precipitated red needle crystals were filtered and washed with 3 ml of mixed solvent of n-hexane and ethyl acetate (3:1).

75 mg of the 3,6-diamino-2,5-pyrazinedicarbonitrile was obtained as red crystal needles (postulating one molecule of the 3,6-diamino-2,5-pyrazinedicarbonitrile is formed from two molecules of DAAN, the yield was 45%).

| | |
|---|---|
| Melting point | >280° C. |
| Mass spectrum: | $M^+ = 160$. |
| Absorption spectrum $\lambda$max: | 223, 266, 458, nm in DME. |
| Fluorescent spectrum $\lambda$em: | 538 nm, |
| | ($\lambda$ex: 460 nm in DME). |
| $^{13}$C-NMR spectrum: | 149.730, |
| | 115.115, |
| | 113.251 ppm |
| | (d$_6$-DMSO). |
| HRMASS spectrum | |
| found | 160.0495 |
| calculated ($C_6H_4N_6$) | 160.0497. |

EXAMPLE 2

Instead of DAAN, reacting 400 mg of 2,3-diamino-3-(4-chloro-phenylthio)-acrylonitrile in the same manner as in Example 1 with bubbling air, 57 mg of the 3,6-diamino-2,5-pyrazinedicarbonitrile as red crystals was obtained. (yield: 40.3%)

EXAMPLE 3

To a slurry prepared by mixing 120.0 g of DAAN, 1200 ml of acetonitrile, 285 ml of xylene and 4800 ml of water there was added a solution of 6253 ml of 0.1M citric acid and 508 ml of a 0.1M sodium citrate aqueous solution to adjust the pH to be 3.1. The reaction mixture was stirred with bubbling air at 20° C. for 4 hours. Maturing to complete the reaction, red crystals obtained by filtration were washed with 100 ml of water and 150 ml of mixed solvent of n-hexane and ethyl acetate (1:1). After drying at 40° C. for 4 hours, 38.0 g of the 3,6-diamino-2,5-pyrazinedicarbonitrile as red crystals was obtained. (yield: 75.7%).

EXAMPLE 4

To a solution of 6.15 g of DAAN in 76 ml of DME and 457 ml of water were added 70 ml of 1M sodium acetate aqueous solution and 68 ml of a 1M hydrochloric acid aqueous solution to adjust the pH to be 3.7. The reaction was carried out by the same procedures as Example 3. 1.81 g of the 3,6-diamino-2,5-pyrazinedicarbonitrile as red crystals was obtained. (yield: 70.3%).

EXAMPLE 5

To a slurry prepared by mixing 2.05 g of DAAN and 200 ml of chloroform was added 1N hydrochloric acid aqueous solution to adjust the pH to be 3.0. The reaction mixture was stirred with bubbling air at 20° C. for 4 hours keeping the pH at 3.0 with the occasional addition of 1N hydrochloric acid aqueous solution, followed by the same procedures as Example 3. 0.31 g of 3,6-diamino-2,5-pyrazinedicarbonitrile in the form of red crystals was obtained. (yield: 36.2%).

EXAMPLE 6

To a slurry prepared by mixing 6.15 g of DAAN, 76 ml of benzene and 245 ml of water were added 320 ml of 0.1M citric acid and 26 ml of 0.1M sodium citrate aqueous solution to adjust the pH to be 3.0. The reaction mixture was stirred with bubbling air at 20° C. for 4 hours, followed by the same procedures as in Example 3. 1.93 g of the 3,6-diamino-2,5-pyrazinedicarbonitrile as red crystals was obtained. (yield: 75.1%).

EXAMPLE 7

To a solution of 2.05 g of DAAN, 42 ml of acetonitrile and 82 ml of water was added 1N hydrochloric acid aqueous solution and the pH was adjusted to 3.1. The reaction mixture was stirred with bubbling air at 20° C. for 4 hours, followed by the same procedures as in Example 3. 0.57 g of the 3,6-diamino-2,5-pyrazinedicarbonitrile as red crystals was obtained. (yield: 66.5%).

EXAMPLE 8

To a solution of 2.20 g of 2,3-diamino-3-(p-tolylthio)acrylonitrile in 25 ml of DME and 82 ml of water were added 107 ml of 0.1M citric acid and 9 ml of 0.1M sodium citrate aqueous solution to adjust the pH to be 3.2. The reaction mixture was stirred with bubbling air at 20° C. for 4 hours, followed by the same procedures as in Example 3. 0.60 g of the 3,6-diamino-2,5-pyrazinedicarbonitrile as red crystals was obtained. (yield: 69.9%).

EXAMPLE 9

To a solution of 1.62 g of 2,3-diamino-3-(ethylthio)acrylonitrile in 26 ml of DME and 87 ml of water were added 113 ml of 0.1M citric acid and 9.5 ml of a 0.1M sodium citrate aqueous solution to adjust the pH to be 3.2. The reaction mixture was stirred with bubbling air at 20° C. for 4 hours, followed by the same procedures as in Example 3. 0.44 g of the 3,6-diamino-2,5-pyrazinedicarbonitrile as red crystals was obtained. (yield: 48.7%).

EXAMPLE 10-15

The results of syntheses to the invented compound from DAAN as the starting material under various conditions (solvents, buffer solutions, pH and so on) are summarized in Table 1.

TABLE 1

| Example No. | Solvent | Buffer solution | Reacted at 20° C. for 4 hours | |
|---|---|---|---|---|
| | | | pH | Yield(%) |
| 10 | DME | 1 N formic acid + 1 N NaOH | 3.2 | 64.3 |
| 11 | DME | 0.1 N Na citrate + 0.1 N HCl | 2.5 | 61.9 |
| 12 | DME | 0.1 M glycine + 0.1 M NaCl + 0.1 M HCl | 3.4 | 70.8 |
| 13 | methanol | 0.1 M citric acid + 0.1 M Na citrate | 3.0 | 70.1 |
| 14 | acetonitrile | 1 N Na acetate + 1 N HCl | 4.0 | 70.4 |

TABLE 1-continued

| Example No. | Solvent | Buffer solution | Reacted at 20° C. for 4 hours pH | Yield(%) |
|---|---|---|---|---|
| 15 | xylene | 0.1 N citric acid + 0.1 N Na citrate | 3.1 | 70.5 |

EXAMPLE 16

Air was bubbled to a solution of 0.74 g of DAAN oxalate in 75 ml of acetonitrile for 6 hours to complete the reaction. The reaction mixture was concentrated by an evaporator to remove acetonitrile and filtered with adding water. The precipitates was washed with water and successively with a mixed solvent of n-hexane and ethyl acetate (3:2) and dried at 60° C. for 2 hours. 0.10 g of the invented compound was obtained as red crystals. (yield: 47.5%).

EXAMPLE 17

A solution of 191.0 g of DAAN and 68.7 g of picric acid in 4800 ml of acetonitrile was stirred at room temperature for 2.5 hours. Formed reddish crystals were washed with 300 ml of a mixed solvent of n-hexane and ethyl acetate (2:1) and dried at 60° C. for 3 hours. 56.2 g of the 3,6-diamino-2,5-pyrazinedicarbonitrile was obtained as red crystals. (yield: 70.3%)

EXAMPLE 18

To a solution of 2.90 g of DAAN in 50 ml of acetonitrile was added 0.35 g of trifluoroacetic acid at room temperature. The reaction mixture was stirred for 3 hours. Precipitated reddish crystals was filtered and washed with a mixed solvent of n-hexane and ethyl acetate (2:1) and dried at 60° C. for 2 hours. 0.79 g of the 3,6-diamino-2,5-pyrazinedicarbonitrile was obtained as red crystals. (yield: 65.0%).

EXAMPLE 19

A solution of 2.90 g of DAAN and 0.71 g of oxalic acid in a mixed solvent of 75 ml of acetonitrile and 20 ml of water was stirred at room temperature for 3.5 hours. Precipitated reddish crystals were washed with 300 ml of a mixed solvent of n-hexane and ethyl acetate (2:1), and dried at 60° C. for 3 hours. 0.55 g of the 3,6-diamino-2,5-pyrazinedicarbonitrile obtained as red crystals. (yield: 45.4%)

INDUSTRIAL APPLICABILITY

The 3,6-diamino-2,5-pyrazinedicarbonitrile itself is a red pigment and shows powerful yellowish green fluorescence. Therefore, it is possible to apply it as fluorescent dyestuff and light energy conversion material. Additionally, it is a useful intermediate to synthesize pteridines which are widely utilized in the agricultural and pharmaceutical industries.

The methods of preparation of the invention are economically excellent processes. 3,6-diamino-2,5-pyrazinedicarbonitrile, the target compound presented in structural formula [II], is obtained by a one step procedure in high yield from the readily available 2,3-diamino-acrylonitrile derivatives.

We claim:

1. A process for the production of 3,6-diamino-2,5-pyrazinedicarbonitrile, from compounds having the formula

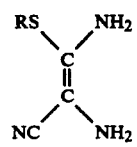

where R is aryl, alkyl, aralkyl or alkenyl, as a starting material, and, reacting said compound in an acidic solution or a solution of the salt(s) of said acidic solution, by bubbling air through the solution for a period of between about 1 to about 12 hours at atmospheric pressure and room temperature with the pH of the solution being kept at from about 1 to about 5.

2. The process of claim 1 wherein the pH is adjusted to 3.0 and the compound is added to a solution of dimethoxyethane and the mixture is allowed to stand for about 5 hours at room temperature, after which precipitated red crystal needles are filtered and washed with a mixed solvent of n-hexane and ethyl acetate in a ratio of about 3:1.

3. The process of claim 1 wherein the compound is 2,3-diamino-3-(4-chloro-phenylthio)-acrylonitrile.

4. The process of claim 1 wherein the acidic solution is a solution of citric acid, and a sodium citrate aqueous solution is employed to adjust the pH to be 3.1.

5. The process of claim 1 wherein the acidic solution is a solution of hydrochloric acid.

6. The process of claim 1 wherein the acidic solution is a solution of picric acid.

7. The process of claim 1 wherein the acidic solution is a solution of trifluoroacetic acid.

8. The process of claim 1 wherein the acidic solution is a solution of oxalic acid.

* * * * *